(12) United States Patent
Ko

(10) Patent No.: US 6,305,980 B2
(45) Date of Patent: Oct. 23, 2001

(54) CABLE END CONNECTOR HAVING ACCURATELY POSITIONED CONNECTION TERMINAL THEREIN

(75) Inventor: David Tso-Chin Ko, Thousand Oaks, CA (US)

(73) Assignee: Hon Hai Precision Ind. Co., Ltd., Taipei Hsien (TW)

( * ) Notice: Subject to any disclaimer, the term of this patent is extended or adjusted under 35 U.S.C. 154(b) by 0 days.

(21) Appl. No.: 09/796,878

(22) Filed: Feb. 28, 2001

(51) Int. Cl.[7] ....................................................... H01R 9/05
(52) U.S. Cl. ............................................. 439/582; 439/585
(58) Field of Search ..................................... 439/578–585

(56) References Cited

U.S. PATENT DOCUMENTS

| | | | |
|---|---|---|---|
| 5,061,206 | * | 10/1991 | Kawanami et al. ................ 439/585 |
| 5,110,308 | * | 5/1992 | Nishikawa et al. ................. 439/585 |
| 5,263,877 | * | 11/1993 | Mitani .................................. 439/585 |
| 5,569,049 | * | 10/1996 | Tatebe et al. ....................... 439/582 |
| 5,603,636 | * | 2/1997 | Kanou et al. ....................... 439/585 |
| 5,772,470 | * | 6/1998 | Togashi ................................ 439/582 |
| 5,785,555 | * | 7/1998 | O'Sullivan et al. ................ 439/585 |
| 5,860,833 | * | 1/1999 | Chillscyzn et al. ................. 439/585 |
| 5,879,190 | * | 3/1999 | Maruyama et al. ................ 439/582 |
| 6,099,350 | * | 8/2000 | Wright ................................. 439/582 |

\* cited by examiner

Primary Examiner—Gary Paumen
(74) Attorney, Agent, or Firm—Wei Te Chung

(57) ABSTRACT

A cable end connector includes a dielectric housing (10), a terminal (30) received in the housing, a shell (50) shielding the housing, and a retainer (60) attached to the shell for holding a coaxial cable (70) therein. The housing includes a tubular portion (20) and a base portion (40) engaged with the tubular portion. The base portion includes a platform (433) projecting from a top surface thereof and a pair of retaining walls (45) projecting along two sides thereof. Each retaining wall defines a groove (453) therein. The terminal has a mating portion (33) supported on said platform and a tail portion (31) secured in the grooves. The shell has a trunk portion (51) enclosing the tubular portion of the housing, and a planar portion (53) connected to the trunk portion for supporting the base portion of the housing.

1 Claim, 7 Drawing Sheets

CABLE END CONNECTOR HAVING ACCURATELY POSITIONED CONNECTION TERMINAL THEREIN

FIELD OF THE INVENTION

The present invention relates to a cable end connector, and more particularly to a cable end connector having a terminal reliably received in the housing.

BACKGROUND OF THE INVENTION

Cable end connectors are often used for transmitting Radio-frequency (RF) signals. The cable end connectors normally have a terminal received in a housing thereof to mate with a complementary plug. Such a conventional cable end connector is, for example, disclosed in U.S. Pat. No. 5,585,877. The cable end connector includes a dielectric member holding a central terminal within an outer conductive shell. The central terminal has a U-shaped connection portion for connecting with a coaxial cable and a coupling portion for mating with a complementary plug. As disclosed in this patent, in assembly, an upper side wall of the dielectric member and a holder portion of the outer shell are bent substantially at a right-angle to hold the connection portion of the terminal and an inner conductor of the coaxial cable within the dielectric member and to crimp the coaxial cable braiding to the connector outer shell.

However, as for this design, the terminal tends to move with respect to the coaxial cable. To prevent the movement, the dielectric member and the shell have to hold the coaxial cable tightly. Thus, the assembly process is complicated.

Hence, an improved connector for firmly fixing a terminal via a housing is required to overcome the disadvantages of the prior art.

The copending application Ser. No. 09/709,226 filed Nov. 8, 2000 with the same inventor and the same assignee, discloses an approach to replace the design of U.S. Pat. No. 5,263,877, and the instant application specifically focuses on the terminal retention issue and the shell/housing retention issue thereof.

BRIEF SUMMARY OF THE INVENTION

A main object of the present invention is to provide a cable end connector having a terminal reliably received in the housing thereof.

Another object of the present invention is to provide a cable end connector having a shell firmly enclosing a housing.

A cable end connector according to the present invention comprises a dielectric housing, a terminal received in the housing, a unitarily formed shell, and a retainer attached to the shell for holding a coaxial cable therein.

The housing includes a base portion and a tubular portion engaged with the base portion. The base portion includes an engaging block and a flat portion extending from the engaging block. The engaging block has a platform projecting from a top surface thereof. Three cutouts are angularly defined in an outer periphery of the engaging block. Two bumps are respectively formed on opposite sides of each cutout. A pair of retaining walls project along opposite sides of the flat portion. A pair of grooves are respectively defined in an inward lower corner of each retaining wall and oppose each other. Three recesses are angularly defined in an outer periphery of the tubular portion. Three mounting legs angularly depend from a bottom of the tubular portion. The legs are respectively received in the corresponding cutouts and abut against the bumps thereby securely fixing the tubular portion to the base portion. The terminal has a mating portion supported on said platform and a tail portion secured in the grooves. The shell comprises a planar portion supporting the housing, and a trunkportion bendably connected to the planar portion and enclosing the tubular portion of the housing. Three retentive tabs are inwardly formed in the trunk portion and received in the recesses of the tubular portion of the housing to press the tubular portion of the housing, thereby securely fixing the tubular portion to the base portion of the housing.

Other objects, advantages and novel features of the invention will become more apparent from the following detailed description when taken in conjunction with the accompanying drawings.

DETAILED DESCRIPTION OF THE INVENTION

Figure 1:
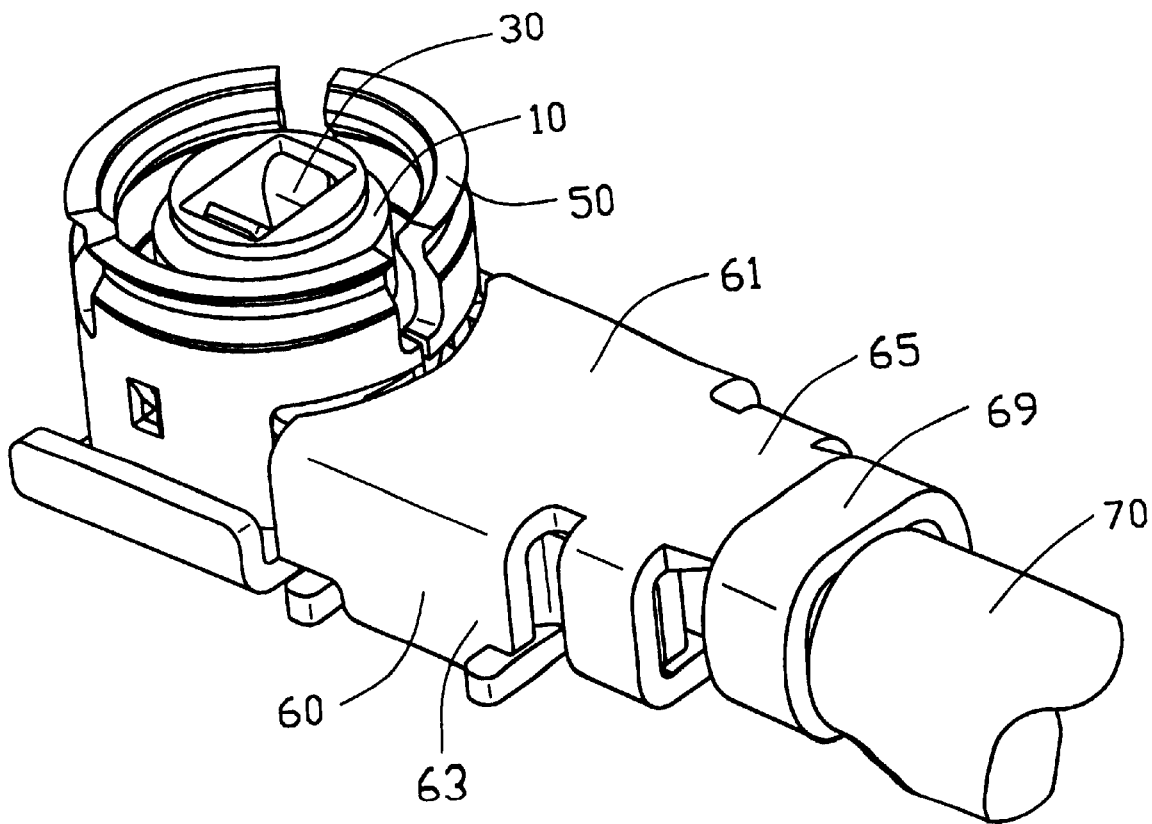
FIG. 1 is a perspective view of a cable end connector assembly of the present invention.
Figure 2:
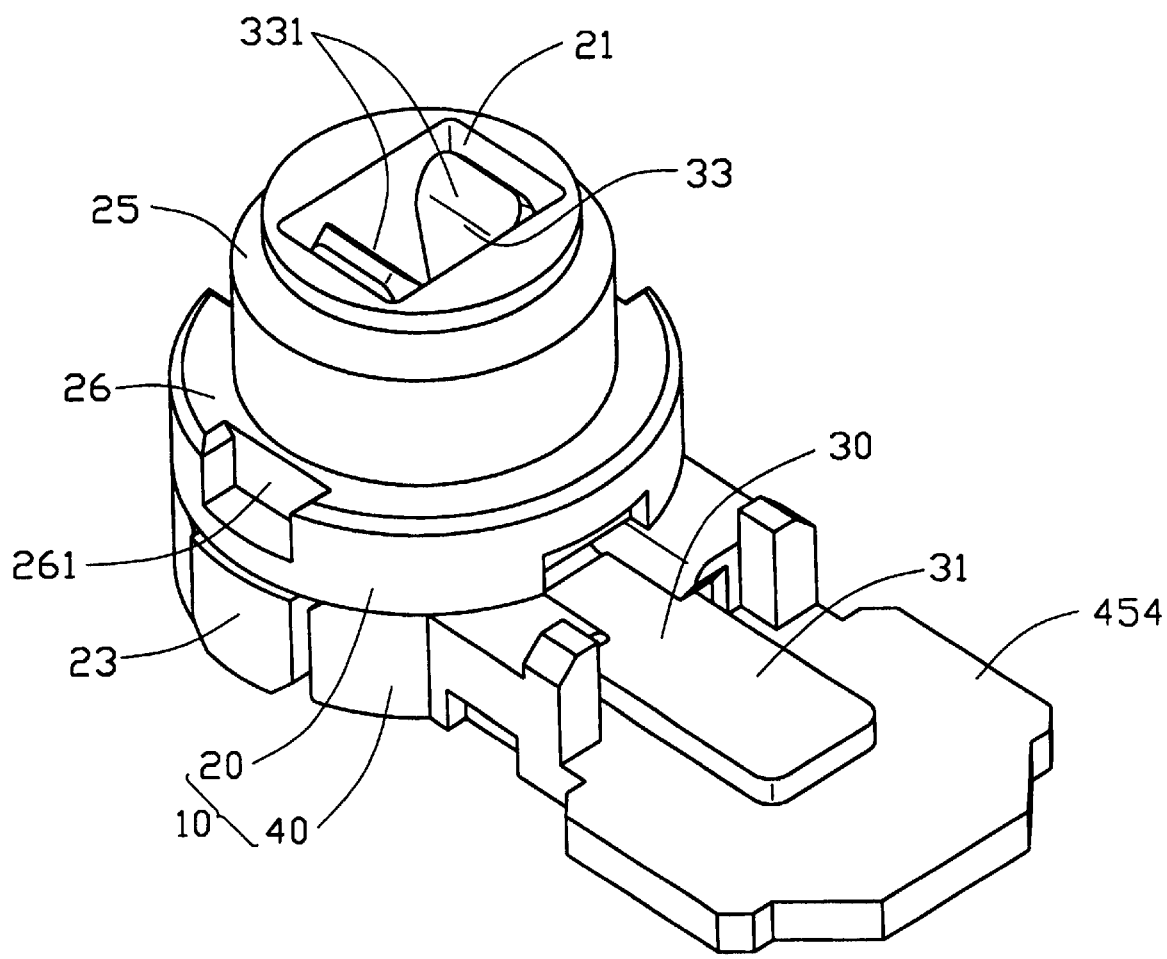
FIG. 2 is a perspective view of a terminal assembled within a housing of the cable end connector according to the present invention.

Referring to the drawings and particularly to FIG. 1, a cable end connector in accordance with the present invention comprises a dielectric housing 10, a terminal 30, a metallic shell 50 shielding the housing 10 and the terminal 30, and a retainer 60 for securing an end portion of a coaxial cable 70.

Referring to FIGS. 2–5, the dielectric housing 10 comprises a tubular portion 20 and a base portion 40 for engaging with the tubular portion 20. A substantially rectangular upper passageway 21 is axially defined through the tubular portion 20.

The tubular portion 20 forms a first step 25 and a second step 26 below the first step 25. Three recesses 261 are angularly disposed in an outer periphery of the second step 26 of the tubular portion 20 and exposed to a top surface of the second step 26. Three mounting legs 23 angularly depend from a bottom of the tubular portion 20 for locking with the base portion 40 and are respectively beneath corresponding recesses 261.

Figure 3:
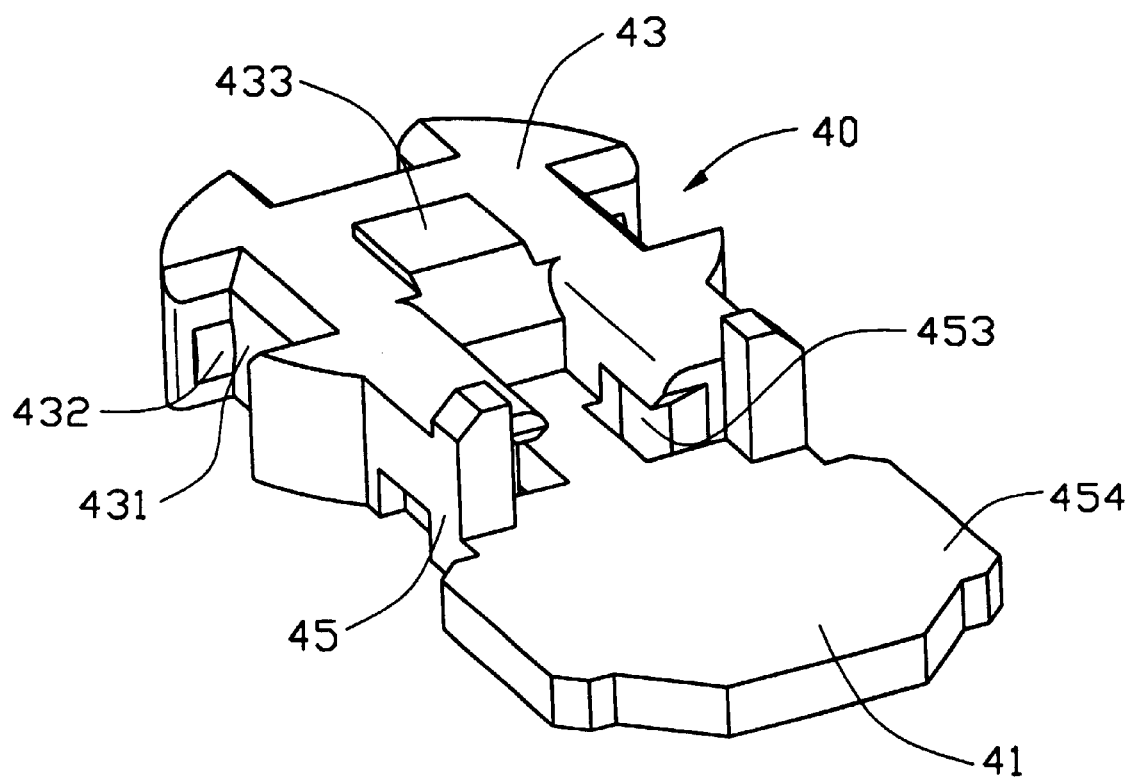
FIG. 3 is a perspective view of a base portion of the housing of the cable end connector.

Particularly referring to FIG. 3, the base portion 40 comprises an engaging block 43 and a flat portion 41 extending rearwardly from the engaging block 43. A substantially rectangular platform 433 protrudes from a top surface of the engaging block 43 for supporting a part of the terminal 30. Three substantially rectangular cutouts 431 are angularly distributed in an outer periphery of the engaging block 43 and dimensioned for retaining the mounting legs 23. Inside each cutout 431 is formed a pair of bumps 432 on opposite sidewalls thereof for firmly retaining the mounting leg 23 of the tubular portion 20. A pair of retaining walls 45 project along opposite sides of the flat portion 41. A pair of grooves 453 are respectively defined in an inward lower corner of each retaining wall 45 and oppose each other. A pair of wings 454 are formed on opposite sides of the flat portion 41 proximate the retaining wall 45.

Figure 4:
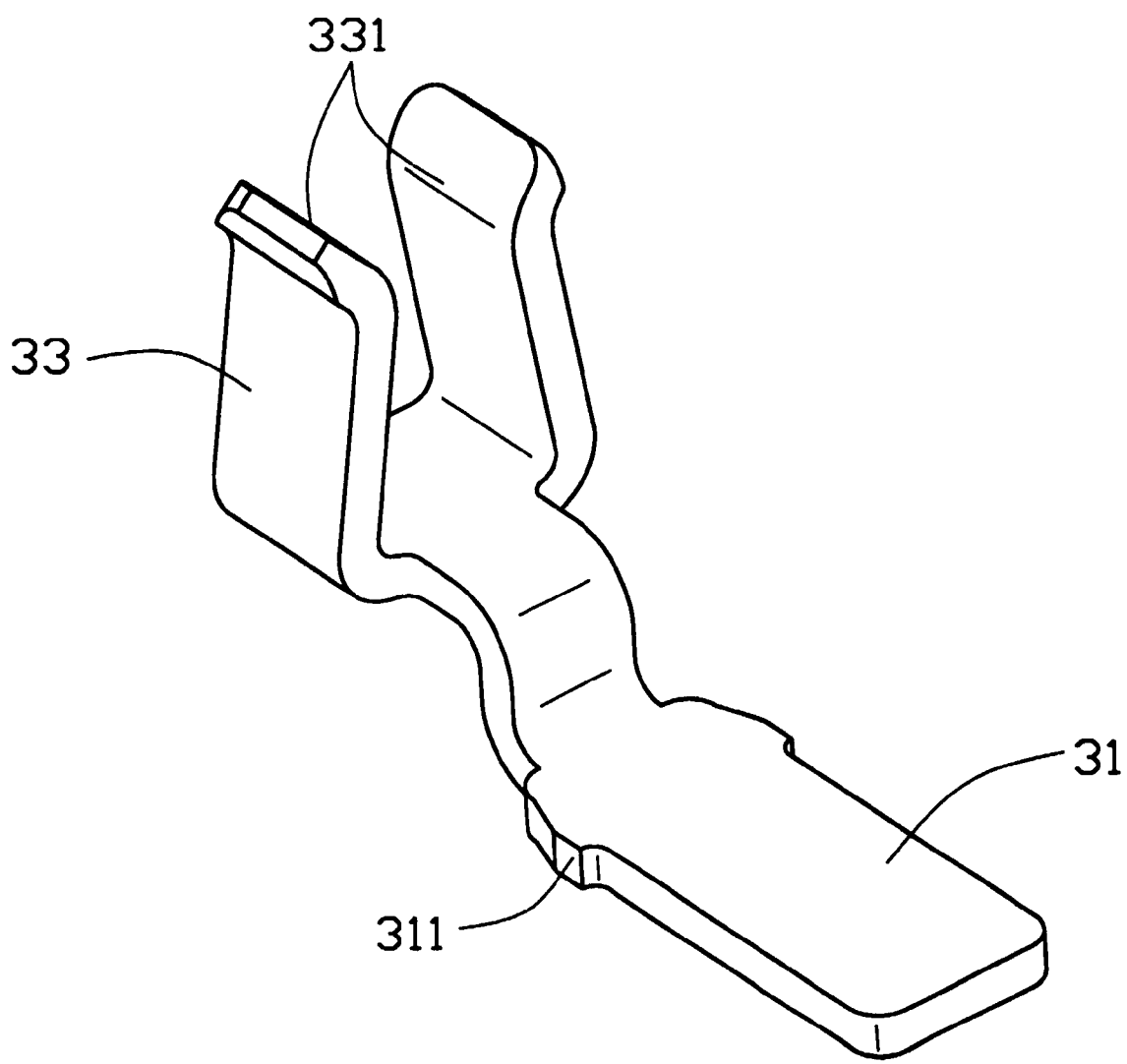
FIG. 4 is a perspective view of a terminal of the cable end connector.
Figure 5:
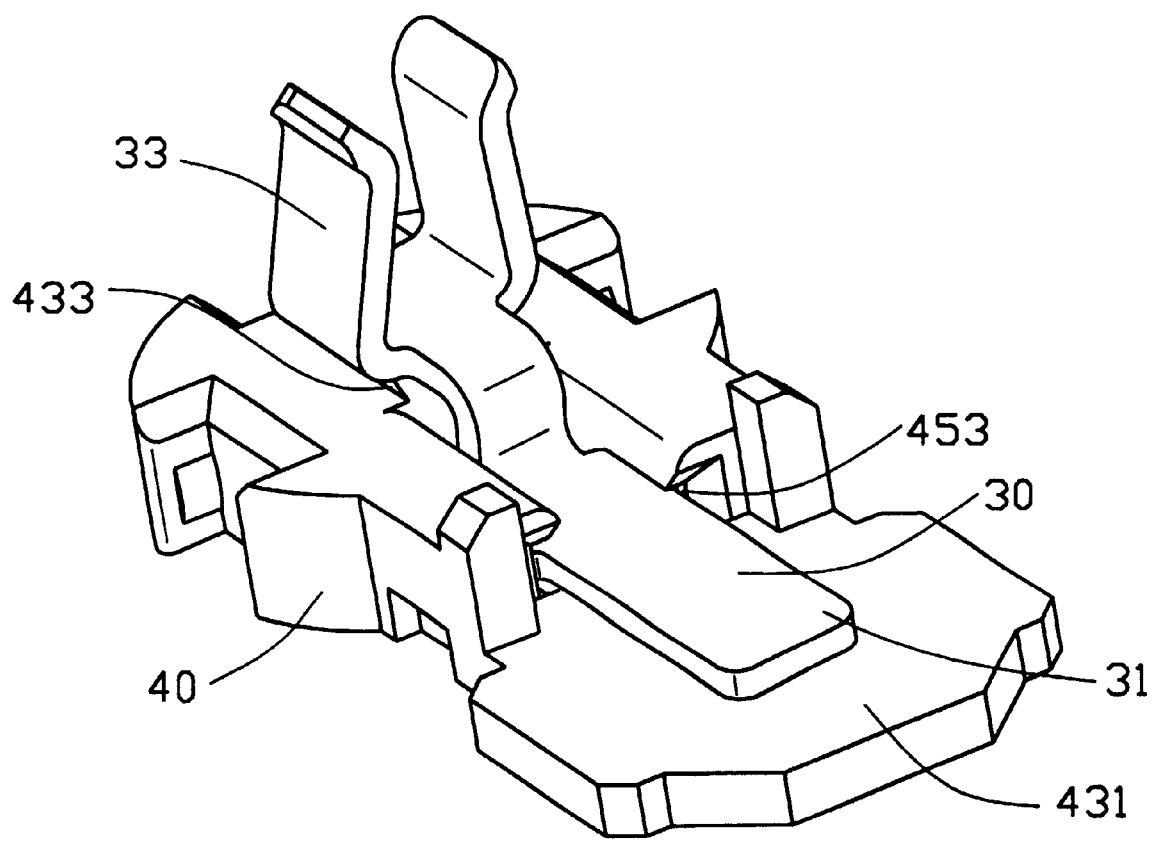
FIG. 5 is a perspective view of the terminal assembled within the base portion of the housing of the cable end connector according to the present invention.

Particularly referring to FIG. 4, the terminal 30 includes a mating portion 33 and a planar tail portion 31 rearwardly extending and offsetting from the mating portion 33. The mating portion 33 is bifurcated and consists of a pair of beams 331 substantially projecting toward each other for mating with a complementary connector (not shown). A barb 311 is formed on each of two opposite sides of the tail portion 31 near the mating portion 33 for being received in corresponding groove 453.

Figure 6:
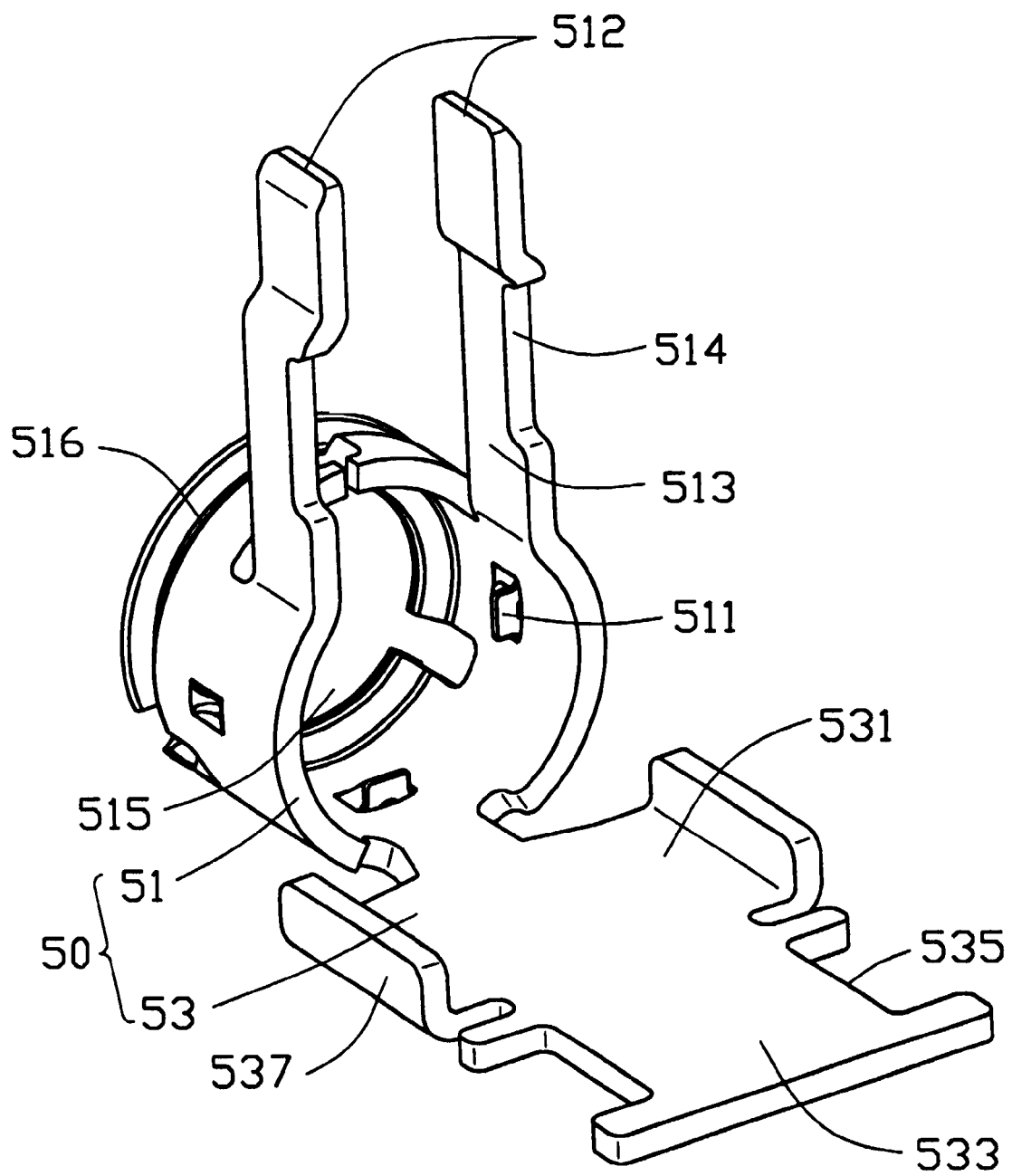
FIG. 6 is a perspective view of a shell of the cable end connector, wherein the shell is unbent.

Referring to FIG. 6, the shell 50 is unitarily formed and comprises a cylindrical trunk portion 51 and a planar portion 53 connected to the trunk portion 51. FIG. 6 shows the shell 50 when the trunk portion 51 is unbent and is approximately perpendicular to the planar portion 53.

The trunk portion 51 has a pair of arms 513 rearwardly extending from a lower portion thereof. Each arm 513 defines a bight 514 in a lower portion thereof for retaining the wings 454 of the base portion 40 of the housing 10. Each arm 513 has an elongate distal end 512 protruding inwardly for accommodating the coaxial cable 70 (see FIG. 7) therebetween. The trunk portion 51 defines a hollow portion 515 therethrough for enclosing the tubular portion 20 of the housing 10. Three retentive tabs 511 angularly and inwardly distributed on the trunk portion 51 for fitting into the recess 261 of the tubular portion 20 of the housing 10 to press the tubular portion 20, thereby securely fixing the tubular portion 20 of the housing 10 to the base portion 40 of the housing 10. An inner step 516 is inwardly formed on the trunk portion 51 for cooperating with the first step 25 of the housing 10.

The planar portion 53 has a front portion 531 for supporting the trunk portion 51, and a rear portion 533 for supporting the arms 513 and the housing 10. The front portion 531 forms a pair of side walls 537 on opposite sides thereof for interferentially fitting with the outer periphery of the trunk portion 51. A pair of elongated notches 535 are respectively defined in opposite sides of the rear portion 533.

With reference to FIG. 1, the retainer 60 is conductive and comprises a planar top wall 61, a braiding crimp 65 rearwardly of the top wall 61 for grounding a braiding layer 75 of the coaxial cable 70 (see FIG. 7), and a strain relief 69 rearwardly of the braiding crimp 65 for securely clamping the coaxial cable 70. A pair of locking tabs 63 respectively depend downward from opposite sides of the top wall 61 for engaging with the notches 535 of the planar portion 53. FIG. 1 shows the retainer 60 in its bended, crimped state. Prior to assembly, it is in an unbended state in which the top wall 61 and locking tabs 63, the braiding crimp 65, and the strain relief 69 all have generally U-shaped cross-sections.

Figure 7:
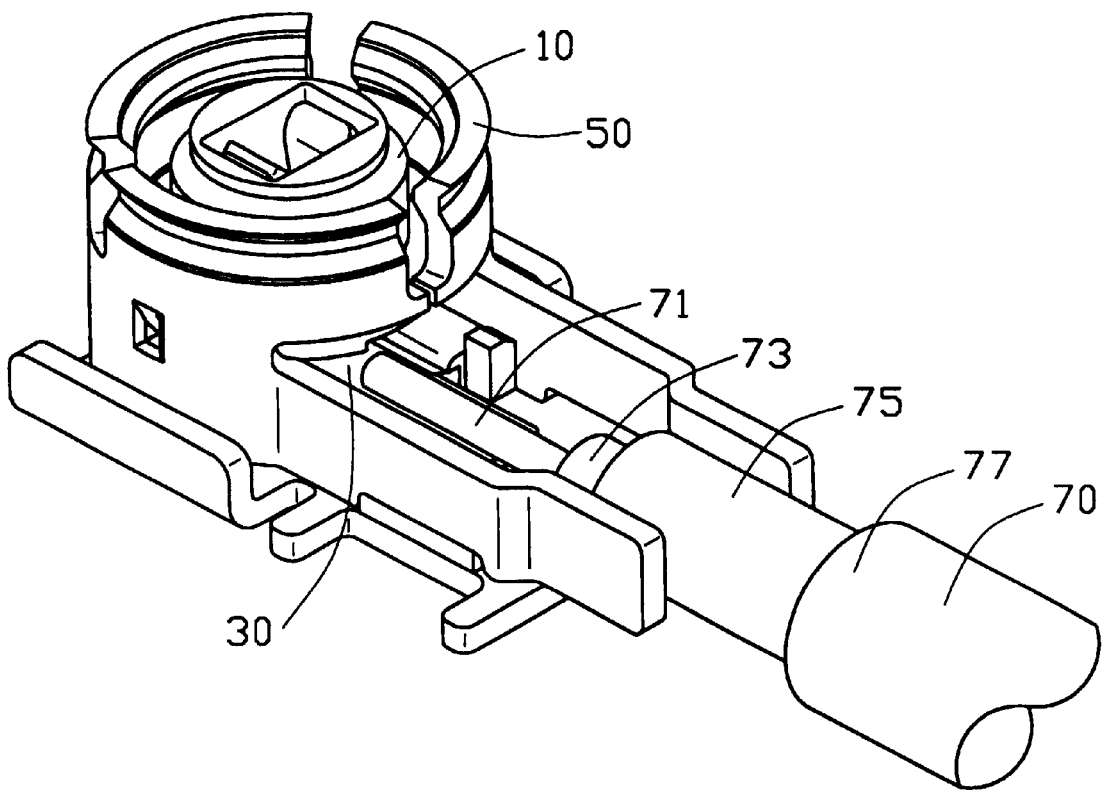
FIG. 7 is a view similar to FIG. 1, wherein a retainer of the cable end connector is removed for clarity.

Particularly referring to FIG. 7, the coaxial cable 70 includes an inner conductor 71, a braiding layer 75, an inner insulator 73 separating the inner conductor 71 and the braiding layer 75 and an outer insulator 77 surrounding the braiding layer 75.

Particularly referring to FIGS. 5, 2, 7 and 1, a cable end connector assembly is assembled as follows.

(1) The tail portion 31 of the terminal 30 is inserted from the flat portion 41 of the base portion 40 of the housing 10. The barbs 311 of the tail portion 31 of the terminal 30 and part of the tail portion 31 are secured in corresponding grooves 453 of the retaining walls 45. The mating portion 33 extends forwardly beyond the retaining walls 45 and then is positioned on the platform 433.

(2) The tubular portion 20 of the housing 10 is mounted onto the base portion 40. The mounting legs 23 fit into corresponding cutouts 431 of the base portion 40 and securely abut against the bumps 432 of the corresponding cutouts 431. The mating portion 33 of the terminal 30 extends into the upper passageway 21 of the tubular portion 20, the beams 331 of the mating portion 33 abutting against corresponding inner walls (not labeled) of the upper passageway 21.

(3) An inner conductor 71 of the coaxial cable 70 is soldered onto the tail portion 31 of the terminal 30.

(4) The trunk portion 51 of the shell 50 is brought to encircle the housing 10, the retentive tabs 511 abutting against the recesses 261. The arms 513 accommodate the flat portion 41 of the housing 10 therebetween.

(5) The planar portion 53 is bent toward the trunk portion 51 until the planar portion 53 completely abuts a bottom of the housing 10.

(6) The locking tabs 63 of the retainer 60 engage with the corresponding notches 535 of the planar portion 53, thereby fixedly retaining the arms 513 to the planar portion 53. The tail portion 31 of the terminal 30 is therefore surrounded by both the arms 513 and the top wall 61 of the retainer 60 but without contacting either. The braiding crimp 65 of the retainer extends beyond the arms 513 of the trunk portion 51 for securely clamping the braiding layer 75 of the coaxial cable 70. The outer insulator 77 of the coaxial cable 70 is firmly retained in the strain relief 69 of the retainer 60.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A cable end connector comprising:

a housing comprising a base portion and a tubular portion engaged with the base portion, the base portion including an engaging block and a flat portion extending from the engaging block, said tubular portion defining at least one recess in an outer periphery thereof;

a terminal received in the housing;

a metal shell including a planar portion attached to a bottom face of the base portion, and a trunk portion connected to said planar portion and enclosing said tubular portion of said housing, said trunk portion having at least one retentive tab received in the at least one recess of the tubular portion to press the tubular portion of the housing, thereby securely fixing the tubular portion to the base portion of the housing; and a discrete retainer attached to said planar portion for retaining a part of the shell to said planar portion, said retainer and the shell surrounding but not contacting said terminal;

wherein the engaging block of the base portion of the housing forms a platform projecting from a top surface thereof, the flat portion forms a pair of retaining walls projecting from two sides thereof, each retaining wall defining a groove therein; and wherein the terminal has a mating portion supported by the platform and a tail portion secured in the grooves;

wherein a pair of barbs are formed on opposite sides of the tail portion of the terminal and latch with the grooves of the housing;

wherein the base portion defines at least one cutout in an outer periphery thereof, and the tubular portion has at least one mounting leg received in the at least one cutout for fixing the tubular portion to the base portion;

wherein each cutout inwardly forms a pair of bumps for abutting against a corresponding leg of the tubular portion of the housing for securely fixing the tubular portion of the housing to the base portion of the housing.

* * * * *